United States Patent [19]

Dahms

[11] Patent Number: 5,300,207
[45] Date of Patent: Apr. 5, 1994

[54] HIGH CURRENT COULOMETRIC KF TITRATOR

[76] Inventor: Harald Dahms, 472 Madison Ave., Toms River, N.J. 08753

[21] Appl. No.: 4,462

[22] Filed: Jan. 14, 1993

[51] Int. Cl.$^5$ ............................................. G01N 27/26
[52] U.S. Cl. ................................ 204/405; 204/153.23; 422/15
[58] Field of Search .................. 204/153.22, 153.23, 204/405; 436/39, 40, 41, 42; 422/75

[56] References Cited

U.S. PATENT DOCUMENTS 4,230,554 10/1980 Blanke .................................. 204/405
5,139,955 8/1992 Scholz ............................. 204/153.22

Primary Examiner—John Niebling
Assistant Examiner—Bruce F. Bell

[57] ABSTRACT

A high current coulometric titrator for the Karl Fischer determination of water in which a diaphragm is not required between the electrodes of the iodine-generating circuit. These electrodes are designed to ensure that substantially only iodine is generated at the anode while minimizing conversion of iodine to iodide at the cathode. In a preferred embodiment, the anode has a generally curved shape, all portions of which are substantially equidistant from the cathode. Increased current efficiency results wherein the amount of iodine generated at the anode increases as the magnitude of the iodine-generating current increases. Titration rates in excess of 2.5 milligrams of water per minute are achieved.

24 Claims, 2 Drawing Sheets

HIGH CURRENT COULOMETRIC KF TITRATOR

DESCRIPTION

Field of the Invention

This invention is a high current coulometric Karl Fischer titrator which operates with high iodine-generating current, and more particularly to such a titrator which provides a high rate of iodine generation wherein the titrator does not require a diaphragm between the electrodes used to generate iodine.

Background Art

Water analysis using the Karl Fischer method for detecting the amount of water in samples is well known in the art. Iodine in a solution combines with water to change the properties of the solution. These property changes can be detected using indicator electrodes, or by using a colorimetric detector.

The Karl Fischer reaction by which the water content of an unknown sample is detected is given by the following expression:

$$I_2 + H_2O + SO_2 + \text{amine} = 2HI + SO_3 \cdot \text{amine} \quad (1)$$

Present Karl Fischer titrators (KF titrators) are of two types: volumetric titrators and coulometric titrators. In a volumetric titrator a known volume of an iodine-containing solution (titrant) is added during titration. In a coulometric titrator, iodine is generated in a vessel solution by passing an electric current between two electrodes (anode and cathode) immersed in the KF solution. At the positive electrode (anode) the following reaction occurs to generate iodine $I_2$:

$$I^- - e^- = \tfrac{1}{2} I_2 \quad (2)$$

Here, iodide ions $I^-$ lose electrons to be converted to iodine $I_2$.

Many instruments are commercially available using both volumetric and coulometric generation of iodine. Generally speaking, volumetric titrators can titrate larger amounts of water faster. Typical rates of titration can be more than 20 milligrams of water per minute. In contrast, coulometric titrators titrate smaller amounts of water more slowly having typical titration rates of about 1-3 milligrams of water per minute. Some coulometric titrators can operate up to about 20 milligrams of water per minute; however, there are problems with such high current titrators and their design is more complicated, requiring a diaphragm between the anode and the cathode as well as multiple solutions in separate compartments in the titrator. The reason for the generally lower rate of titration of coulometric titrators is related to the difficulties of passing a rather high electrical current through the titrator, which will be explained in more detail later. It is usually the situation that coulometric titrators are used for the analysis of low moisture samples (such as solvents and oils) while volumetric titrators are used for analysis of high moisture samples. The reason for this is primarily due to the lower rate of titration available from coulometric titrators.

Coulometric titrators do, however, have some inherent advantages over volumetric titrators. For example, in a coulometric titrator a complex apparatus is not required for delivering a precise volume of liquid and therefore coulometric titrators have an advantage of technical simplicity.

Further, the accuracy of a coulometric titrator can be greater than that of a volumetric titrator since the iodine-generating current is easily measurable as compared to using a titrant whose strength can change prior to use. Of course, coulometric titrators do not need the additional titrant solution which is in itself an advantage.

It would be generally desirable to have a coulometric titrator which provides a high titration rate comparable to the titration rate of volumetric titrators, but which would be a more simple apparatus without the need for a diaphragm between the anode and the cathode. The provision of such an apparatus is primary object of this invention.

In coulometric titrators, an electric current is passed through a solution in a vessel where the solution typically includes $SO_2$, a buffer (such as amine), iodide ions ($I^-$), and a solvent. At the anode the reaction described in equation 2 occurs to generate iodine. However, at the cathode a number of unknown electrolysis products are generated. These unknown reaction products can react with the iodine which is formed at the anode so that a portion of the generated iodine is consumed in reactions with the products generated at the cathode. This is undesirable, as it would make the analyzer inaccurate since it would then be difficult to know what fraction of the iodine is consumed by the water in the unknown sample, or by a reaction with an unknown product formed at the cathode.

In order to prevent reactions between the products formed at the cathode and the iodine formed at the anode, existing high current coulometric analyzers use a diaphragm between the anode and the cathode. The diaphragm separates these two electrodes and keeps the cathodic reaction products out of the main reaction cell so that they don't undergo reactions with the iodine. The diaphragm separates the vessel into two compartments but allows electrical current to flow through it. As diaphragms, fritted (porous) glass disks are commonly used, but certain plastic ion exchange membranes can also be used. The function of the diaphragm is to restrict flow between the anode and cathode while allowing electric current to pass therethrough.

The use of such diaphragms has disadvantages. The diaphragms may clog when certain substances such as oil are analyzed for water content. Also, diaphragms become especially problematical when higher currents are passed between the cathode and the anode. In particular, currents in excess of 400 mA will pull more interfering species through the diaphragm, thereby allowing undesirable reactions between the generated iodine and species other than the water in the unknown sample.

Because of the foregoing problems with diaphragms and presently known coulometric titrators, the use of low currents (100-300 mA) allows a structure to be built without the need for a diaphragm. However, such titrators tend to be very slow as they generate very small amounts of iodine at the anode. On the other hand, high current titrators which generate large amounts of iodine at the anode require a diaphragm in order to have improved accuracy (i.e., to prevent reaction products from consuming the generated iodine).

The present invention solves these problems by providing an improved structure which will generate large amounts of iodine at the anode while minimizing the formation of products other than iodine at the anode. This new structure is a high current coulometric titrator which can operate in the current range of 500 mA–20 A without the need for a diaphragm separating the anode and the cathode. This structure ensures that at least about 95% of the reaction products produced at the anode are iodine, thereby minimizing the occurrence of secondary reactions between these reaction products and iodine. The provision of such an improved structure is based on a recognition that the current paths between the cathode and the anode in a coulometric titrator are critical to the generation of species other than iodine at different locations along the anode. By providing substantially equal current path distances between the cathode and the anode, the anode produces substantially only iodine at large rates of generation without the need for a diaphragm to prevent undesirable reactions.

Therefore, it is an object of the present invention to provide an improved high current coulometric titrator for KF water determinations.

It is another object of this invention to provide a high current coulometric titrator for KF water determinations which does not require the use of a diaphragm between the anode and the cathode of the apparatus, even though currents in excess of 500 mA are used to generate iodine therein.

It is another object of this invention to provide a high current coulometric titrator for KF water determinations having electrode means which ensures that substantially only iodine is produced at the anode.

It is another object of this invention to provide an improved coulometric titrator for KF water determinations which will carry currents in excess of about 500 mA, where the reaction products other than iodine produced at the anode are less than about 5% of the total of the reaction products produced thereat.

It is another object of the present invention to provide a high current coulometric titrator for KF water determinations having a high rate of titration with improved accuracy.

It is another object of this invention to provide a high current coulometric titrator for KF water determinations in which the efficiency of $I_2$ generation increases as the iodine generating current increases.

It is another object of this invention to provide an improved coulometric titrator for Karl Fischer water analysis which can provide a titration rate in excess of 2.5 milligrams of water per minute without the need for a diaphragm.

BRIEF SUMMARY OF THE INVENTION

The improved coulometric titrator of the present invention is one whose electrode structure allows the passage of very high currents (>500 mA) between the cathode and the anode used to generate iodine in the reaction vessel, with a minimum production of products other than iodine at the anode. Even though high currents, typically in the range 500 mA–20 A, can be used to rapidly generate iodine, a diaphragm is not required to separate the iodine-generating electrodes. This eliminates the disadvantages attendant to the use of a diaphragm while at the same time providing a titrator which can titrate samples having large water amounts. The iodine-generating efficiency of this titrator is improved over prior art high current coulometric titrators (which must use a diaphragm), and the accuracy of the present titrator is greater than those presently known, since the production of reaction products other than iodine at the anode is minimized.

The titrator generally comprises a reaction vessel filled with a single KF solution, in which a cathode and an anode operate as the iodine-generating electrodes. The cathode is preferably small, approximating a point source. The anode is a larger area electrode which generally surrounds the cathode and is of a shape and geometry such that the current paths from the cathode to the anode are substantially equal over the entire anode. This ensures that substantially the only reaction product at the anode is iodine, even when very high currents are used between the cathode and the anode.

The vessel solution is comprised of a reducing agent, such as $SO_2$, a buffer (such as amine), iodide ions ($I^-$) and a solvent. These KF solutions are well known in the art. A particularly good solution is one made by the Riedeldehaen Company of Seelze, Germany, which is called HYDRANAL Coulomat AD, catalog number 34810.

These and other objects, features, and advantages will be apparent from the following more particular description of the preferred embodiments.

DETAILED DESCRIPTION OF THE PREFERRED EMBODIMENTS

Figure 1A:
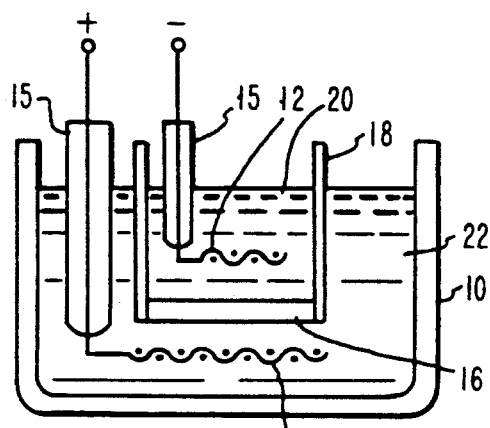
FIGS. 1A and 1B schematically illustrate coulometric titrators of the type known in the art, where the titrator of FIG. 1A uses a high current but requires a diaphragm, while the titrator of 1B does not require a diaphragm but uses very low currents.
Figure 1B:
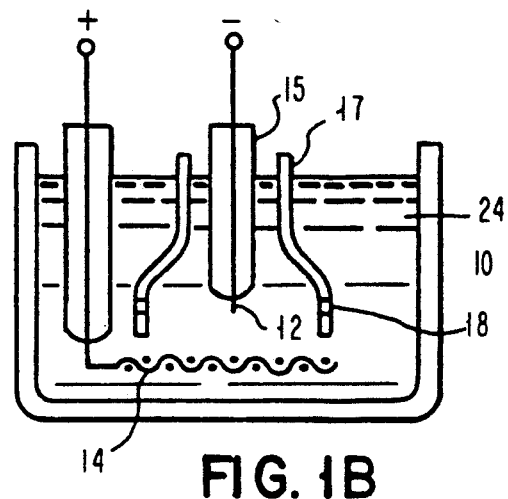

FIGS. 1A and 1B illustrate two types of coulometric titrators of the types that are commercially available. FIG. 1A is a representation of a model AF7 coulometric titrator available from Orion Research, Boston. This type of titrator can use iodine-generating currents of up to about 4A, but requires a diaphragm between the electrodes. The diaphragm is required because the large current pulls ions through the diaphragm so that the current efficiency is not 100%. In this context, current efficiency relates to the percentage of the electric current which is used to generate iodine at the anode. The titrator is comprised of the reaction vessel 10, a flat porous cathode 12, a flat porous anode 14, and a diaphragm 16 located between the cathode 12 and the anode 14. Cathode 12 and anode 14 are generally sealed in glass tubes 15. Diaphragm 16 is typically a fritted (porous) glass or a porous plastic membrane. It is connected to the glass tube 18 which divides the reaction vessel into two compartments. A first solution 20 is located in the inner compartment within glass tube 18 while a second solution 22 is located in the main reaction compartment, i.e., the compartment in which the sample having an unknown water content is introduced.

In practice, the separation between the cathode and anode is not complete and the electric current therebetween pulls certain species through the membrane 16.

This makes the analysis inaccurate since consumption of iodine can occur other than by reaction of iodine and water in the unknown sample. As noted previously, the use of such diaphragms has further disadvantages, such as clogging, and the increased passage of adverse species therethrough especially when higher currents are used.

FIG. 1B shows another type of commercially available coulometric titrator which does not require a diaphragm. This titrator is representative of a type (Model 684) sold by Metrohm AG of Herisau, Switzerland. This titrator uses a special anode and cathode and a special solution which seems to limit the reaction products produced at the cathode. However, the titrator of FIG. 1B is used only at very low currents, typically less than 300 mA. This results in a low titration rate of less than 2 milligrams of water per minute.

In FIG. 1B, the same reference numerals are used for components which function the same as those represented in FIG. 1A. Accordingly, reaction vessel 10 has therein a pointed tip cathode 12 and a generally flat, porous anode 14. Cathode 12 is sealed in an insulating material 15, such as glass. The KF solution 24 is HYDRANAL Coulomat AD and has a catalog number 34810. It is made and sold by Riedeldehaen of Seelze, Germany. In this design, the surface area of the cathode is small (less than about 1 square cm.) to minimize the production of interfering cathode products and also to limit reactions in which iodine combines with electrons at the cathode to produce iodide ions. The primary reaction product at the cathode is hydrogen ($H_2$), which is channeled to the surface of the KF solution by the glass tube 17. Openings 18 in tube 17 allow circulation of the KF solution. Because the iodine-generating current is so small, the titrator of FIG. 1B has a very low titration rate and its application is limited to the analysis of samples having very small water content.

As noted, as the electric current is increased in order to generate more iodine and therefore to allow higher titration rates, reaction products produced at the cathode and the anode are more likely to form. Secondary reactions between the generated iodine and these additional reaction products, wherever formed, lead to inaccuracies. That is, the consumption of iodine will occur through reactions other than with the water in the unknown sample.

It is also desirable that 100% of the electric current be used to generate iodine at the anode. In a general sense, this can never be exactly reached. One reason for this is that small amounts of iodine are reduced back to iodide ions at the cathode.

In the practice of the present invention, applicant has discovered that the high currents between the cathode and the anode must travel substantially equal current paths in order that substantially only iodine be produced at the anode. Further, applicant has discovered that the use of his improved electrode structures provides the surprising result of increasing the current efficiency as the magnitude of the iodine-generating current is increased. This increased efficiency will also lead to increased accuracy even though no diaphragm is used in the titrator.

Figure 2:
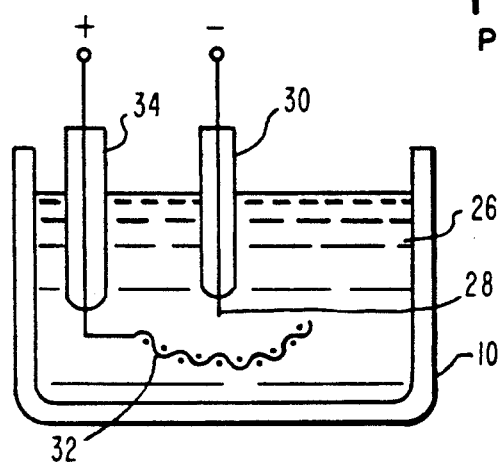
FIG. 2 schematically illustrates one embodiment of the present invention where a high current titrator is provided without the need for a diaphragm.

FIG. 2 schematically illustrates an embodiment of the present invention to provide an improved high current coulometric titrator that does not require a diaphragm. In FIG. 2, the reaction vessel 10 is filled with a KF solution 26, which could be the aforementioned HYDRANAL solution, or another KF solution. The cathode 28 is illustrated as a pointed tip cathode comprising, for example, a platinum wire enclosed or sealed in a glass sleeve 30. The cathode area in this embodiment is very small. The anode 32 is of generally spherical shape surrounding the exposed tip 28. Anode 32 has a portion thereof enclosed or sealed by a glass sleeve 34. The anode is generally a platinum wire gauze or mesh supported by platinum wire. In a preferred embodiment, the ratio of cathode area to anode area is less than about 1:10.

Since the exposed portion of anode 32 has a generally spherical shape all portions of it are located at approximately the same distance from the cathode tip 28. This means that substantially all the current paths from the tip 28 to the exposed regions of the anode 30 will be approximately constant. At very high currents this will ensure that substantially only iodine will be formed along the entire exposed length or area of the anode. In this manner in excess of 95% of the reaction product at the anode will be iodine, even if very high currents flow between the cathode and the anode.

It will be appreciated that in FIG. 2 a side view is shown. The anode 32 can be an area electrode that is a portion of a sphere in order that all portions of it are substantially equidistant from the tip of the cathode 28. Further, the anode is generally below the cathode so that iodine created at the anode will not be carried to the cathode when the solution 26 is stirred, as by a magnetic stirrer bar located at the bottom of vessel 10. In a practical titrator, it is usually the case that the cathode is not located in the area of high iodine concentration since iodine can combine with electrons at the cathode to produce iodide ions. As mentioned, this adversely affects the accuracy of the analysis. Of course, configurations where the cathode is not necessarily located above the anode may be envisioned if the stirring mechanism is such that the generated iodine is not brought to the cathode. Also, while semispherical anodes are particularly suitable, the anode can be less than, or even greater than one-half a sphere. The precise anode shape and geometry are chosen in accordance with the cathode design to provide the equidistant current paths.

Figure 3:
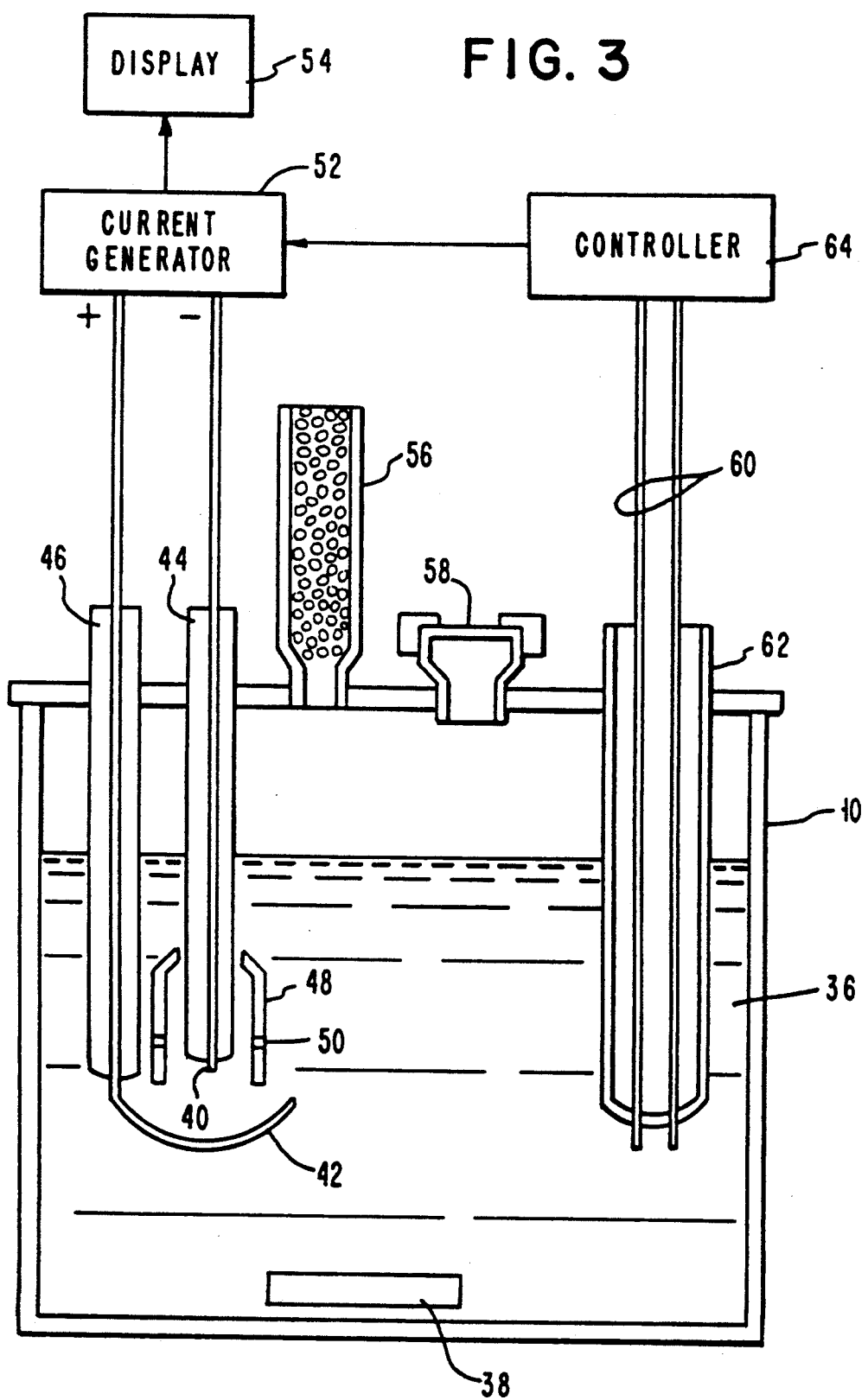
FIG. 3 is an illustration of a more complete coulometric titrator using the iodine generating electrode structure schematically illustrated in FIG. 2.

FIG. 3 illustrates a more complete embodiment of the titrator of this invention. Here, the vessel 10 contains a KF solution 36 and a magnetic stir bar 38. The iodine-generating electrodes are the cathode 40 and the anode 42. Cathode 40 is generally a platinum wire sealed in a glass sleeve 44, while another glass sleeve 46 is used to seal a portion of the anode 42. The exposed portion of anode 42 is generally spherical and located about the pointed cathode 40 such that substantially equal length current paths exist between the cathode 40 and the exposed regions of the anode 42. A glass tube 48 is located in the general vicinity of the cathode 40 and is used to channel gaseous products (hydrogen) generated at the cathode to the surface of the KF solution 36. Small holes 50 are made in glass tube 48 to allow circulation of the KF solution.

Cathode 40 and anode 42 are connected to an electric current generator 52 which can be attached to a display 54 for indication of the magnitude of the iodine-generating current between the cathode 40 and the anode 42. A drying tube 56 is located at the top of the titrator, as is a septum 58 which is used for introduction of the unknown sample into vessel 10. Indicator electrodes 60, sealed in glass tube 62, are used to measure the iodine left in the solution 36 after titration in order to indicate the amount of water present in the sample. Electrodes 60 are connected to a controller 64 which is in turn connected to the current generator 52.

In a particular construction of the titrator of FIG. 3, the anode 42 was formed as a semispherical anode having a radius of 2 cm. The anode was made from platinum wire gauze supported by platinum wire. Cathode 40 was a platinum electrode sealed in glass with only a 4 mm tip exposed to the KF solution 36. The cathode tip was placed in the center of the semispherical platinum anode.

In operation, a high current was provided from a 12 volt current source through a variable resistor and an on-off switch. Whenever the switch was closed a timer was actuated to time the duration of the current flowing through the cell. The indicator electrodes 60 were connected to a power supply set at 300 millivolts in series with a 50 microampere d.c. meter. In one test, the KF solution was the aforementioned HYDRANAL coulomat solution. The iodide content and the conductivity of the solution where increased by adding 0.25 moles of iodine and 0.25 moles of water per liter.

The titrator of FIG. 3 was used to analyze water-containing samples by first titrating to zero water content by generating iodine in the cell. This was accomplished by passing current from the cathode to the anode until the indicator meter showed a current of 25 microamperes. This indicated that the KF solution 36 contained a small amount of iodine. The water sample was then added through the septum 58 and the iodine generating current was switched on until the endpoint of 25 microamperes was again reached on the indicating meter. The amount of water in the sample could then be computed from the time and current passed between the indicator electrodes 60, according to Faraday's law.

The relationship between electric current and the rate of analysis in coulometry is governed by Faraday's law, which is well known to those skilled in the art. Based on this law, a current of 1A theoretically generates 78.4 milligrams of iodine that in turn react with 5.6 milligrams of water. Hence it can be stated that a titrator with a current of 400 mA has a titration rate of 2.2 milligrams of water, one with a current of 500 mA has a titration rate of 2.8 milligrams of water, etc. All these rates are per minute.

The current strength for generating iodine was varied by setting the variable resistor to different values. A range of 400 mA-5A was tested, as were higher ranges. Excellent results were achieved without the need for a diaphragm.

In this testing an unusual effect was observed which was unexpected. This related to the current efficiency that was obtained. While the ideal current efficiency for the generation of iodine in a coulometric titrator is 100% (i.e., 100% of the current is used to generate iodine at the anode), this theoretical maximum is never exactly reached. One reason is that small amounts of iodine are reduced back to iodide at the cathode. Other reasons relate to the production of species other than iodine at the anode.

The effects of increasing the iodine-generated current were studied to determine current efficiency. Known amounts of water were added to the analyzer and the analysis was performed each time according to the procedure described hereinabove. The following table shows the results.

TABLE 1

| Current | Current efficiency |
| --- | --- |
| 100 mA | 95% |
| 300 mA | 95.5% |
| 500 mA | 98% |
| 800 mA | 98% |
| 1000 mA | 98% |
| 2000 mA | 98% |

The results of these efficiency tests indicate that there is an increase in current efficiency as the iodine-generating current is increased. This is surprising, since it would be expected that the current efficiency would decrease as the iodine-generating current is increased. This increased current efficiency provides increased accuracy of the titrator as the iodine-generating current is increased. Further, the increased accuracy of the titrator was achieved without the use of a diaphragm between the cathode and the anode.

Figure 4:
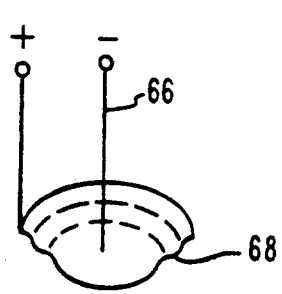
FIGS. 4, 5, and 6 illustrate additional electrode arrangements which can be utilized in the practice of the present invention.
Figure 5:
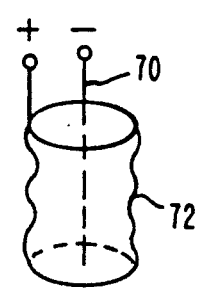
Figure 6:
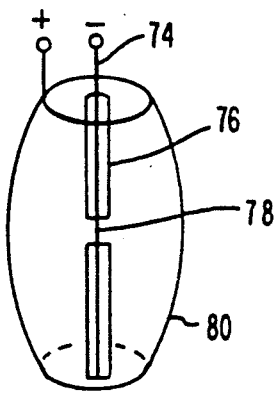

FIGS. 4–6 illustrate some additional embodiments of the electrode structure used to generate iodine in the titrator. In FIG. 4, the cathode 66 is an axial wire whose tip is located in the center of a generally cylindrical anode 68. The glass sleeves in which the cathode and anode are generally sealed are not shown for ease of illustration. Cylindrical anode 68 can be made of a platinum gauze or mesh, the cylindrical anode being open at the top and bottom.

In FIG. 5, the cathode 70 is also a platinum wire which is located axially in the center of a cylindrical anode 72. The anode is usually a platinum wire or mesh. In this embodiment, a substantial portion of the length of cathode 70 is used to conduct current from the cathode radially to the anode 72. With such a structure, it is desirable to have the stirring mechanism be such that iodine produced at the anode is swept axially by the stirring action so that large quantities will not travel to the cathode. The electrode structure of FIG. 5 is not as commercially practical as that of the other embodiments, absent a stirring mechanism which prevents movement of the generated iodine to the cathode. Since the exposed portion of the cathode has substantial length, the risk of iodide generation at the cathode is increased.

In FIG. 6, the cathode 74 is a platinum wire encased in a glass sleeve 76, where there is an exposed portion 78 that is not encased in glass. The anode 80 is generally cylindrical with the maximum diameter of the cylinder occurring in a plane surrounding the exposed portion 78 of the cathode. This ensures that the current paths from the cathode to all portions of the anode are approximately the same length. As in previous designs, the anode can be a platinum gauze or mesh. By minimizing the exposed area of the cathode and by carefully controlling the stirring action in the cell, it is possible to minimize the amount of iodine which converts to iodide at the cathode.

In the practice of this invention, a titrator has been described which minimizes the formation of reaction products other than iodine at the anode, and which has increased current efficiency and accuracy even though very high iodine-generating currents are used and even though no diaphragm is located between the cathode and the anode. While the invention can be varied in form, it is recognized that the use of a very small cathode will provide advantages as described hereinabove. It is also recognized that, while many different types of KF solutions can be utilized, some solutions may be preferable, for example in the limitation of reaction products at the cathode. The present coulometric titrator is designed for high current use without a diaphragm, without sacrificing accuracy and in fact providing increased accuracy. These advantages are particularly unique at currents of at least 500 mA and titration rates in excess of about 2.5 milligrams of water per minute.

While the invention has been described with respect to particular embodiments therein, it will be appreciated by those of skill in the art that variations can be made therein without departing from the spirit and scope of this high current coulometric Karl Fischer titrator.

I claim:

1. A diaphragm-free coulometric titrator for high current Karl Fishcer water determinations, comprising:
   electrode means for producing iodine including a non-consumable anode and a cathode which are immersed in a Karl Fischer solution when said titrator is in use, said cathode and said anode being separated by only said Karl Fischer solution during titration,
   electrical means for producing an electrical current in excess of about 500 mA between said cathode and said anode to generate iodine at said anode and
   indicator electrodes for providing a measure of the iodine content of said Karl Fischer solution, said indicator electrodes being located away from the electrical current paths between said anode and said cathode.

2. The titrator of claim 1, where said electrical means produces currents between said cathode and said anode in the range of about 500 mA–20 A.

3. The titrator of claim 1, where the area of said cathode exposed to said Karl Fischer solution is less than about one tenth the area of said anode exposed to said Karl Fischer solution.

4. The titrator of claim 3, where said cathode is a point electrode while said anode is an area electrode.

5. The titrator of claim 3, where all areas of said anode exposed to said solution are substantially equidistant from said cathode.

6. The titrator of claim 3, where the electrical current paths between said cathode and said anode are substantially equal in length.

7. A diaphragm-free coulometric titrator for water determinations using a Karl Fischer reaction to determine the water content of a sample, comprising:
   iodine-generating means for generating iodine in a Karl Fischer solution, said iodine-generating means including a non-consumable anode and a cathode which are immersed in said solution when said titrator is in use, said anode and said cathode being separated by only said Karl Fischer solution, and
   electrical means for producing an electrical current in excess of about 500 mA between said anode and said cathode for producing iodine at said anode, wherein the electrical current paths between said cathode and said anode through said Karl Fischer solution are substantially equal in length.

8. The titrator of claim 7, where said cathode is a point electrode surrounded by said anode.

9. The titrator of claim 8, where said anode is generally spherically disposed about said cathode.

10. The titrator of claim 7, where said cathode has an area less than the area of said anode and wherein said anode is a curved anode regions of which are at approximately the same distance from said cathode.

11. The titrator of claim 10, further including indicator electrodes for providing a measure of the iodine content of said Karl Fischer solution, said indicator electrodes being located away from the electrical current paths between said anode and said cathode.

12. A diaphragm-free high current coulometric titrator for Karl Fischer water determinations comprising
   a single compartment vessel for holding a Karl Fischer solution,
   non-consumable and anode electrodes both located in said single compartment vessel for carrying electrical current through said Karl Fischer solution to generate iodine at said anode.
   means for minimizing the production of reaction products other than iodine at all regions of said anode when currents in excess of about 500 mA flow between said cathode and said anode, and
   electrical means for producing an electrical current between said cathode and said anode in excess of about 500 mA.

13. The titrator of claim 12, where said electrical current between said cathode and said anode is greater than about 1 A.

14. The titrator of claim 12, where said electrical means produces currents between said cathode and anode in the range of about 500 mA–20 A.

15. A diaphragm-free high current coulometric titrator for Karl Fischer water determinations, comprising
   electrode means for producing iodine including a cathode and a non-consumable anode which are immersed in a Karl Fischer solution when said titrator is in use,
   electrical means for producing an electrical current through said Karl Fischer solution between said cathode and said anode to generate iodine at said anode, said electrical current being in excess of about 500 mA, and
   wherein the electrical current paths between said cathode and said anode are substantially equal in length.

16. The titrator of claim 15, where said electrical means produces currents between said cathode and said anode in the range of about 500 mA–20 A.

17. The titrator of claim 15, where said cathode has an area that is less than the area of said anode, said anode being generally curved in shape and surrounding said cathode.

18. The titrator of claim 17, where said anode has a shape approximating a portion of a sphere.

19. The titrator of claim 17, futher including indicator electrodes for providing an indication of the iodine content of said Karl Fischer solution and stirring means for stirring said solution during titration.

20. A coulometric titrator for water determination using a Karl Fischer reaction, said titrator including:
   iodine generating means for generating iodine in a Karl Fischer solution, said iodine generating means being comprised of a non-consumable anode and a cathode between which an electrical current flows through said Karl Fischer solution to generate iodine at said anode, said anode being curved and having all of its area located equidistant from said cathode, and
   electrical current generating means for providing an electrical current between said cathode and said anode of greater than about 500 mA.

21. A diaphragm-free coulometric titrator for Karl Fischer water determinations, comprising:

electrode means for producing iodine including a cathode and a non-consumable anode which are immersed in a Karl Fischer solution when said titrator is in use, said cathode and said anode being separated by only said Karl Fischer solution, indicator electrodes for providing a measure of the iodine content of said Karl Fischer solution, said indicator electrodes being located away from the electrical current paths between said anode and said cathode, and electrical means for producing an electrical current between said cathode and said anode sufficient to produce a titration rate in said titrator in excess of 2.5 milligrams of water per minute.

22. The titrator of claim 21, where said anode is curved, all portions of said anode being substantially equidistant from said cathode.

23. The titrator of claim 22, where said anode is generally spherical in shape having an area greater than about 10 times as large as the area of said cathode.

24. The titrator of claim 23, where said electrical current between said cathode and said anode is greater than about 500 mA.

* * * * *